United States Patent
Weber et al.

(10) Patent No.: US 11,110,255 B2
(45) Date of Patent: *Sep. 7, 2021

(54) MEDICAL DEVICE WITH SUPPORT MEMBER

(71) Applicant: BOSTON SCIENTIFIC SCIMED, INC., Maple Grove, MN (US)

(72) Inventors: Daniel C. Weber, Plymouth, MN (US); Ross Olson, Anoka, MN (US); Adam D. Grovender, Maple Grove, MN (US); Brian Cornwell, Big Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/847,806

(22) Filed: Apr. 14, 2020

(65) Prior Publication Data

US 2020/0254224 A1    Aug. 13, 2020

Related U.S. Application Data

(63) Continuation of application No. 14/817,903, filed on Aug. 4, 2015.

(Continued)

(51) Int. Cl.
*A61M 25/09* (2006.01)
*A61M 25/00* (2006.01)

(52) U.S. Cl.
CPC .......... *A61M 25/09* (2013.01); *A61M 25/005* (2013.01); *A61M 25/0012* (2013.01);
(Continued)

(58) Field of Classification Search
None
See application file for complete search history.

(56) References Cited

U.S. PATENT DOCUMENTS

| | | | |
|---|---|---|---|
| 3,452,742 | A | 7/1969 | Muller |
| 4,832,047 | A | 5/1989 | Sepetka et al. |

(Continued)

FOREIGN PATENT DOCUMENTS

| | | |
|---|---|---|
| EP | 2732846 A1 | 5/2014 |
| GB | 1119158 A | 7/1968 |
| WO | 9839049 A1 | 9/1998 |

OTHER PUBLICATIONS

International Search Report and Written Opinion dated Nov. 11, 2015 for International Application No. PCT/US2015/043634.

*Primary Examiner* — Patrick Fernandes
*Assistant Examiner* — Benjamin S Melhus
(74) *Attorney, Agent, or Firm* — Seager, Tufte & Wickhem LLP

(57) ABSTRACT

The invention provides design, material, manufacturing method, and use alternatives for medical devices. An example medical device includes an elongate shaft having a distal region and a coil disposed along the distal region. The coil is formed from a winding member having a first filar region and a second filar region. The winding member has a first cross-sectional diameter along the first filar region, a second cross-sectional diameter different from the first cross-sectional diameter along the second filar region, a first centroid at a first position along the first filar region and a second centroid at a second position along the second filar region. The first centroid and the second centroid are axially-aligned.

19 Claims, 12 Drawing Sheets

Related U.S. Application Data

(60) Provisional application No. 62/040,251, filed on Aug. 21, 2014.

(52) U.S. Cl.
CPC ............ *A61M 2025/09108* (2013.01); *A61M 2025/09191* (2013.01)

(56) References Cited

U.S. PATENT DOCUMENTS

| | | |
|---|---|---|
| 4,854,330 A | 8/1989 | Evans, III et al. |
| 4,991,588 A | 2/1991 | Pflueger et al. |
| 5,147,317 A | 9/1992 | Shank et al. |
| 5,238,004 A | 8/1993 | Sahatjian et al. |
| 5,253,653 A | 10/1993 | Daigle et al. |
| 5,354,257 A | 10/1994 | Roubin et al. |
| 5,470,330 A | 11/1995 | Goldenberg et al. |
| 5,551,444 A | 9/1996 | Finlayson |
| 5,606,981 A | 3/1997 | Tartacower et al. |
| 5,833,631 A | 11/1998 | Nguyen |
| 5,865,767 A | 2/1999 | Frechette et al. |
| 6,132,389 A | 10/2000 | Cornish et al. |
| 6,508,803 B1 | 1/2003 | Horikawa et al. |
| 6,620,114 B2 | 9/2003 | Vrba et al. |
| 6,648,874 B2 | 11/2003 | Parisi et al. |
| 7,077,811 B2 | 7/2006 | Vrba et al. |
| 7,182,735 B2 | 2/2007 | Shireman et al. |
| 7,331,973 B2 | 2/2008 | Gesswein et al. |
| 7,494,474 B2 | 2/2009 | Richardson et al. |
| 7,618,379 B2 | 11/2009 | Reynolds et al. |
| 7,637,874 B2 | 12/2009 | Terashi et al. |
| 7,699,792 B2 | 4/2010 | Hofmann et al. |
| 7,744,545 B2 | 6/2010 | Aimi et al. |
| 7,850,623 B2 | 12/2010 | Griffin et al. |
| 8,002,715 B2 | 8/2011 | Shireman |
| 8,043,232 B2 | 10/2011 | Osborne |
| 8,109,888 B2 | 2/2012 | Terashi et al. |
| 8,231,551 B2 | 7/2012 | Griffin et al. |
| 8,262,588 B2 | 9/2012 | Miyata et al. |
| 8,378,011 B2 | 2/2013 | Eramo, Jr. et al. |
| 8,551,133 B2 | 10/2013 | Watanabe et al. |
| 8,585,613 B2 | 11/2013 | Nagano et al. |
| 8,613,713 B2 | 12/2013 | Delaney |
| 8,652,119 B2 | 2/2014 | Nishigishi |
| 8,951,210 B2 | 2/2015 | Miyata et al. |
| 8,956,310 B2 | 2/2015 | Miyata et al. |
| 10,188,413 B1 | 1/2019 | Morriss et al. |
| 2002/0042582 A1 | 4/2002 | Vrba et al. |
| 2004/0039308 A1 | 2/2004 | Murayama et al. |
| 2004/0082879 A1 | 4/2004 | Klint |
| 2004/0093010 A1 | 5/2004 | Gesswein et al. |
| 2004/0122340 A1 | 6/2004 | Vrba et al. |
| 2004/0167442 A1 | 8/2004 | Shireman et al. |
| 2005/0154371 A1 | 7/2005 | Miyata et al. |
| 2005/0267385 A1 | 12/2005 | Hofmann et al. |
| 2005/0273020 A1 | 12/2005 | Whittaker et al. |
| 2006/0100602 A1 | 5/2006 | Klint |
| 2006/0111649 A1 | 5/2006 | Zhou |
| 2006/0122537 A1 | 6/2006 | Reynolds et al. |
| 2006/0167384 A1 | 7/2006 | Kato |
| 2006/0264784 A1 | 11/2006 | Lupton |
| 2006/0271135 A1 | 11/2006 | Minar et al. |
| 2007/0010762 A1 | 1/2007 | Ressemann et al. |
| 2007/0100285 A1 | 5/2007 | Griffin et al. |
| 2007/0213689 A1 | 9/2007 | Grewe et al. |
| 2007/0282225 A1 | 12/2007 | Terashi et al. |
| 2008/0004546 A1 | 1/2008 | Kato |
| 2008/0039823 A1 | 2/2008 | Shimogami et al. |
| 2008/0146967 A1 | 6/2008 | Richardson et al. |
| 2008/0161727 A1 | 7/2008 | Aimi et al. |
| 2008/0194992 A1 | 8/2008 | Satou et al. |
| 2008/0200839 A1 | 8/2008 | Bunch et al. |
| 2009/0005706 A1 | 1/2009 | Miyata et al. |
| 2009/0076416 A1 | 3/2009 | Treacy et al. |
| 2009/0112127 A1 | 4/2009 | Keating et al. |
| 2009/0182246 A1 | 7/2009 | Kinoshita et al. |
| 2009/0299332 A1 | 12/2009 | Shireman |
| 2009/0312747 A1 | 12/2009 | Delaney |
| 2010/0057053 A1 | 3/2010 | Terashi et al. |
| 2010/0069794 A1 | 3/2010 | Uihlein |
| 2010/0145308 A1 | 6/2010 | Layman et al. |
| 2010/0249654 A1 | 9/2010 | Elsesser et al. |
| 2010/0318065 A1 | 12/2010 | Miyata et al. |
| 2011/0082443 A1 | 4/2011 | Griffin et al. |
| 2011/0319872 A1 | 12/2011 | Kawasaki |
| 2011/0319923 A1 | 12/2011 | Watanabe et al. |
| 2012/0029476 A1 | 2/2012 | Kanazawa |
| 2012/0041420 A1 | 2/2012 | Nagano et al. |
| 2012/0041421 A1 | 2/2012 | Nishigishi |
| 2012/0089126 A1 | 4/2012 | Miyata et al. |
| 2012/0089127 A1 | 4/2012 | Miyata et al. |
| 2012/0191070 A1 | 7/2012 | Nishigishi |
| 2012/0253321 A1 | 10/2012 | Tsunezumi |
| 2012/0265100 A1 | 10/2012 | Maki |
| 2012/0323145 A1 | 12/2012 | Nagano et al. |
| 2013/0046285 A1 | 2/2013 | Griffin et al. |
| 2013/0110002 A1 | 5/2013 | Miyata et al. |
| 2014/0031719 A1 | 1/2014 | Kanazawa |
| 2014/0142557 A1 | 5/2014 | Kosugi et al. |
| 2014/0163420 A1 | 6/2014 | Kosugi |
| 2014/0236125 A1 | 8/2014 | Watanabe et al. |
| 2014/0323918 A1 | 10/2014 | Miyata et al. |
| 2014/0358169 A1 | 12/2014 | Terashi et al. |
| 2015/0238734 A1 | 8/2015 | Kanazawa |
| 2016/0001048 A1 | 1/2016 | Koike |

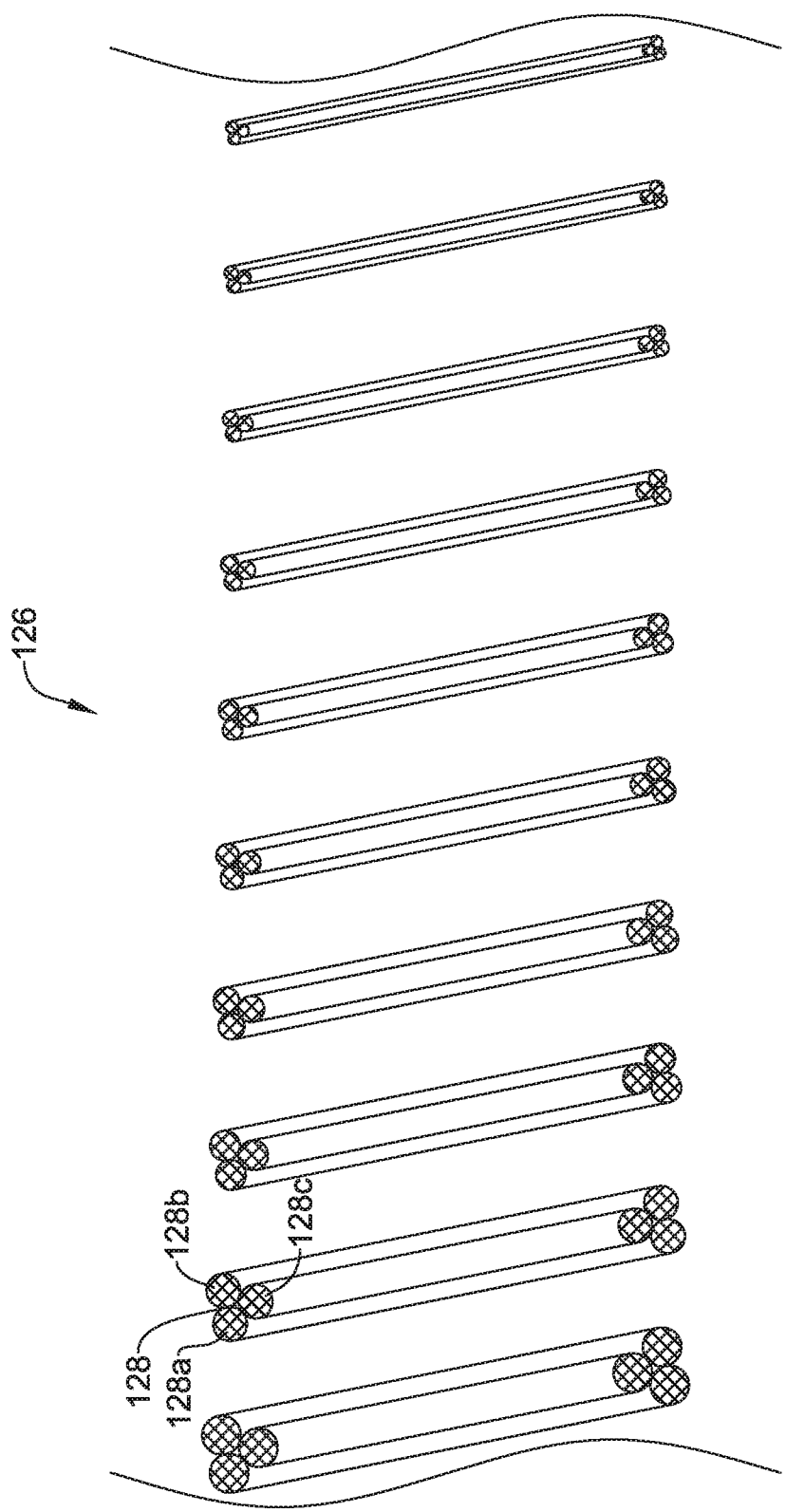

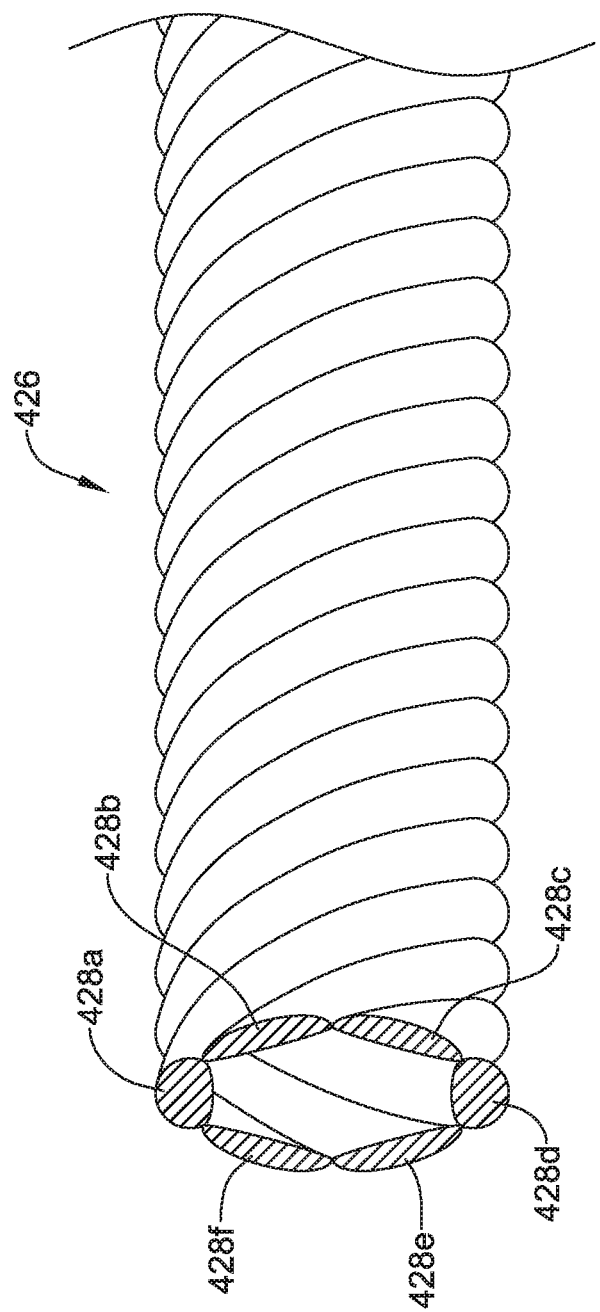

MEDICAL DEVICE WITH SUPPORT MEMBER

CROSS-REFERENCE TO RELATED APPLICATIONS

This application is a continuation of U.S. patent application Ser. No. 14/817,903, filed Aug. 4, 2015, which claims priority under 35 U.S.C. § 119 to U.S. Provisional Application Ser. No. 62/040,251, filed Aug. 21, 2014, the entirety of which are incorporated herein by reference.

TECHNICAL FIELD

The present disclosure pertains to medical devices, and methods for manufacturing medical devices. More particularly, the present disclosure pertains to elongated intracorporeal medical devices including a tubular member connected with other structures, and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes an elongate shaft having a distal region and a coil disposed along the distal region. The coil is formed from a winding member having a first filar region and a second filar region. The winding member has a first cross-sectional diameter along the first filar region, a second cross-sectional diameter different from the first cross-sectional diameter along the second filar region, a first centroid at a first position along the first filar region and a second centroid at a second position along the second filar region. Further, the first centroid and the second centroid are axially-aligned.

Alternatively or additionally to any of the examples above, in another example the first filar region includes a first filar inside diameter and the second filar region includes a second filar inside diameter and the first filar inside diameter is different from the second filar inside diameter.

Alternatively or additionally to any of the examples above, the winding member includes a first pitch in the first filar region and the winding member includes a second pitch in the second filar region, and the first pitch is different than the second pitch.

Alternatively or additionally to any of the examples above, the first pitch is approximately equal to the first cross-section diameter.

Alternatively or additionally to any of the examples above, the coil includes an outer layer.

Alternatively or additionally to any of the examples above, the outer layer substantially surrounds the winding member of the second filar region.

Alternatively or additionally to any of the examples above, the outer layer is capable of altering the flexibility of the first filar region, the second filar region, or both.

Alternatively or additionally to any of the examples above, the first filar region has a first flexibility and the second filar region has a second flexibility and the first flexibility is different from the second flexibility.

Alternatively or additionally to any of the examples above, the winding member has a first outer diameter along the first filar region, and the winding member has a second outer diameter different from the first outer diameter along the second filar region.

Alternatively or additionally to any of the examples above, the first filar region includes a first filar inside diameter and the second filar region includes a second filar inside diameter and the first filar inside diameter is different from the second filar inside diameter.

Alternatively or additionally to any of the examples above, the winding member includes one or more filars.

Alternatively or additionally to any of the examples above, the outer layer includes a proximal outer diameter and a distal outer diameter, and the proximal outer diameter is greater than the distal outer diameter.

Alternatively or additionally to any of the examples above, the first outer diameter of the first filar region is greater than the second outer diameter of the second filar region.

Alternatively or additionally to any of the examples above, the first outer diameter of the first filar region and the second outer diameter of the second filar region decrease step-wise.

Alternatively or additionally to any of the examples above, the outer layer includes a proximal portion and a distal portion, and the outer layer is tapered from the proximal portion to the distal portion.

An example method for manufacturing a medical device includes disposing a coil in a processing solution. The coil is formed from a filar having a cross-sectional diameter. Disposing a coil in a processing solution reduces the cross-sectional diameter of at least a portion of the filar. The method also includes disposing the processed coil along a catheter shaft and securing the coil to the catheter shaft.

Alternatively or additionally to any of the examples above, the processing solution includes acid etching, electropolishing, or both.

Alternatively or additionally to any of the examples above, disposing the coil in the processing solution further includes defining the duration the coil is dipped, the temperature of the processing solution, or both.

Alternatively or additionally to any of the examples above, the filar has a first filar region and a second filar region, and wherein the first filar region includes a first filar inside diameter and the second filar region includes a second filar inside diameter and the first filar inside diameter is different from the second filar inside diameter.

Alternatively or additionally to any of the examples above, the first filar region has a first centroid and the second filar region has a second centroid, and the first centroid is axially-aligned with the second centroid.

Alternatively or additionally to any of the examples above, the first filar region includes a first pitch and the second filar region includes a second pitch, and the first pitch is different from the second pitch.

Alternatively or additionally to any of the examples above, the coil has an outer diameter and reducing the cross-sectional diameter of at least a portion of the filar includes reducing the outer diameter of the coil.

Alternatively or additionally to any of the examples above, securing the coil to the catheter shaft includes disposing a sleeve on the coil.

Alternatively or additionally to any of the examples above, securing the coil to the catheter shaft includes embedding the coil in a coating.

Another example medical device includes a catheter including an inner elongate layer, a coil, and an outer elongate layer. The coil is disposed between the inner layer and the outer layer. The coil defines a distal winding region. The distal winding region includes a first filar region and a second filar region, and the coil has a first cross-section diameter along the first filar region and the coil has second cross-section diameter different from the first cross-section diameter along the second filar region and the outer layer substantially surrounds the coil along the second filar region.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 5 is a cross-sectional view of a multi-strand wire useful in the invention showing a reduction in the diameter of each strand of the multi-strand wire;

FIG. 5a is a side-view of an example multi-strand wire showing flattened cross-sections of individual filars;

Figure 1:
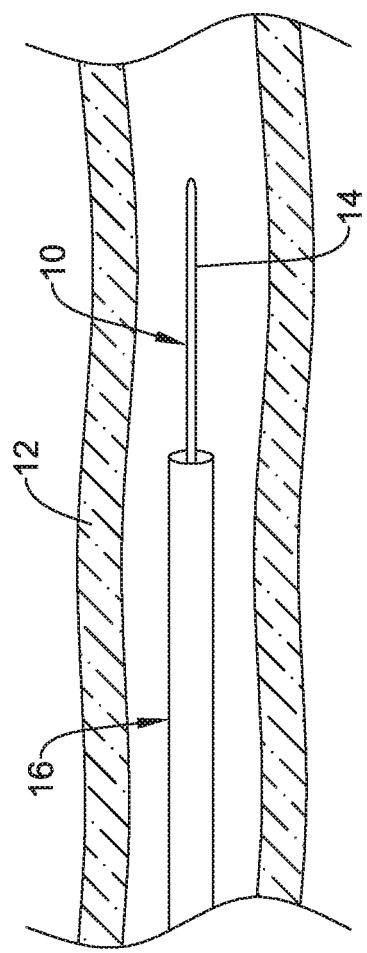
FIG. 1 is a plan view of an embodiment of a medical device according to the invention disposed in a blood vessel.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure.

DETAILED DESCRIPTION

For the following defined terms, these definitions shall be applied, unless a different definition is given in the claims or elsewhere in this specification. All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an embodiment of a medical device 10, for example a guidewire, disposed in a blood vessel 12. Guidewire 10 may include a distal section 14 that may be generally configured for probing within the anatomy of a patient. Guidewire 10 may be used for intravascular procedures. For example, guidewire 10 may be used in conjunction with another medical device 16, which may take the form of a catheter, to treat and/or diagnose a medical condition. Of course, numerous other uses are known amongst clinicians for guidewires, catheters, and other similarly configured medical devices.

Figure 2:
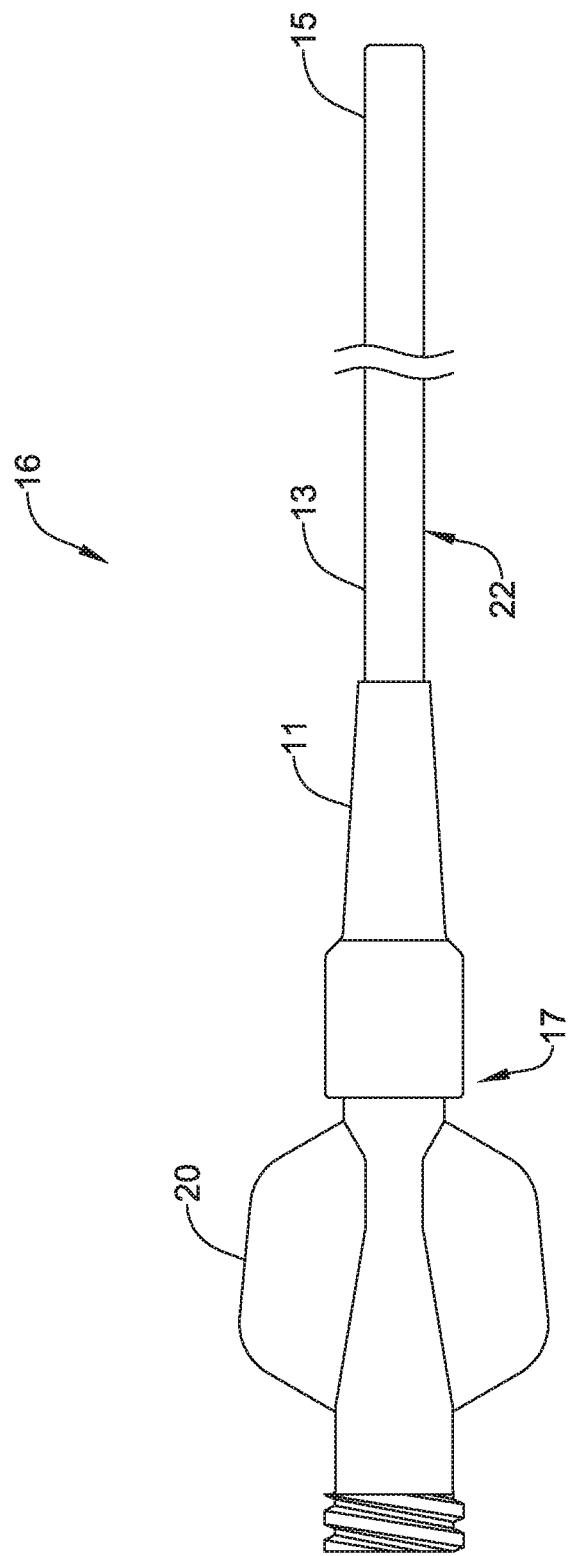
FIG. 2 is an embodiment of a medical device according to the invention.

Although medical device 10 is depicted in FIG. 1 as a guidewire, it is not intended to be limited to just being a guidewire. Indeed, medical device 10 may take the form of other suitable guiding, diagnosing, or treating device (including catheters, endoscopic instruments, laparoscopic instruments, etc., and the like) and it may be suitable for use at other locations and/or body lumens within a patient. For example, FIG. 2 illustrates an embodiment of device 16 in the form of a catheter. Catheter 16 may include a generally elongate shaft 22 having a proximal portion 13 and a distal portion 15. A proximal manifold 17 may be disposed at proximal portion 13. Manifold 17 may include a hub 20 and strain relief 11.

Because of their intended use in the vasculature, some medical devices are designed to have particular physical characteristics such as flexibility (e.g., for the purposes of this disclosure, flexibility may be also be termed or expressed as bending stiffness or flexural rigidity). For example, some medical devices may be designed to be very stiff in order to provide enough columnar strength to navigate anatomical areas of resistance. Alternatively, some medical devices may be designed flexible enough in order to bend in a manner sufficient to traverse tortuous anatomy.

Therefore, at the distal end of the medical device, it may be desirable to tailor the flexibility of the medical device so that the device can effectively reach its target within the vasculature. For example, in order to reach coronary vessels and/or vessels near the heart a guidewire may be designed to be relatively flexible at the distal end. However, if the flexibility is too great, the guidewire may not efficiently turn nor maintain the ability to negotiate a blocked passageway, but instead, may have a tendency to buckle upon itself. Thus, tailoring the flexibility at the distal end of a guidewire so that it is able to efficiently advance through tortuous anatomy while minimizing the likelihood that the guidewire will buckle back upon itself may be desirable.

In some instances it may be desirable to combine different structural components in order to achieve the desired flexibility and stiffness characteristics of a guidewire. For example, it may be desirable to combine (e.g. weld, melt, bond, etc.) one or more different shaft configurations (e.g. different materials, dimensions, etc.) and/or coil configurations with one another to achieve a desired performance output. However, combining different structural components may require a longer and more complex manufacturing process. Therefore, in some instances it may be desirable to tailor and integrate single-piece components into a finished medical device in order that they exhibit desired performance properties. For example, removing material from a single-piece catheter shaft or coil may provide the same benefit as combining two or more non-tailored components. The tailored component may then be integrated into the overall catheter design.

Figure 3:
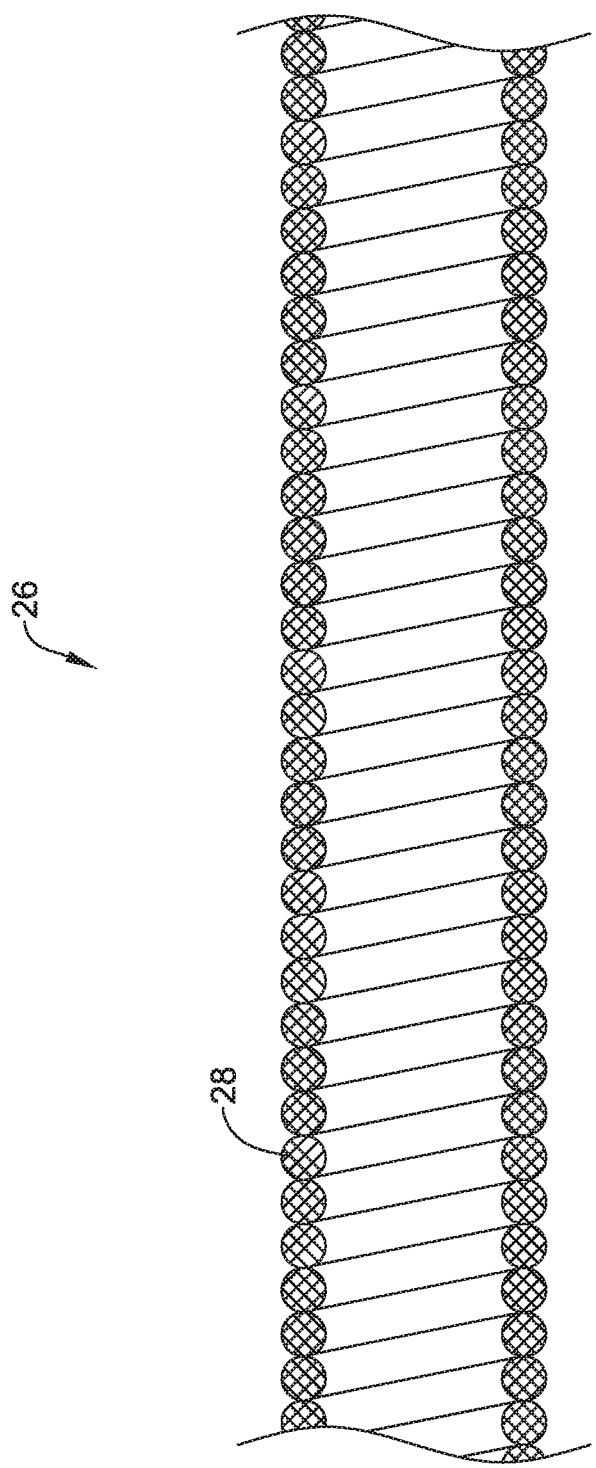
FIG. 3 is a cross-sectional view of a support member useful in the invention.

FIG. 3 shows an embodiment of a support member 26 that may be utilized in catheter 16 and/or other devices disclosed herein. In this embodiment, support member 26 may take the form of a coil. However, in other embodiments, support member 26 may take the form of a braid or other support member. Coil 26 may include one or more filars 28. For purposes of this discussion, a "filar" may be understood as a wire or wires that are wound into a coiled configuration in order to form or otherwise define coil 26. As can be seen in FIG. 3, filar 28 may have a uniform cross-sectional diameter and pitch. While a uniform cross-sectional diameter is shown in FIG. 3, it is contemplated that the cross-sectional diameter of filar 28 may vary across the length of coil 26. Additionally, coil 26 may be configured to have an open pitch, a closed pitch or combinations thereof. For example, FIG. 3 shows filar 28 arranged such that there is no space between the individual windings. The absence of space between the windings may be referred to as a "closed" pitch configuration. A closed pitch configuration may be desirable to provide increased column strength to a given component of a medical device. Further, characteristics such as the filar cross-sectional dimension and/or shape, material, orientation and spacing may contribute to the overall configuration and performance (e.g. flexibility, pushability, trackability, column stiffness, etc.) of coil 26.

As stated above, in some instances in may be desirable to perform a manufacturing process to tailor the design configuration of a medical device component. For example, it may be desirable to alter coil 26 in order to provide the desired flexibility characteristics to catheter 16. For example, it may be desirable to remove material from a distal region of coil 26. In some instances, the manufacturing process may include dipping coil 26 into a processing solution. The dipping process may be done for a given length of time and at a given temperature. For example, processing techniques such as acid etching and/or electropolishing may be utilized, however, similar techniques are contemplated as well. As stated, the amount of material removed from coil 26 may be influenced by the type of solution utilized, the temperature of the solution, the concentration of the solution, the speed/rate at which the coil is dipped, the duration of time the coil is left in the solution, or combinations thereof. Additionally, after having removed material, the shape of coil 26 may be further refined by manipulating the shape of filar 28. For example, filar 28 may be "re-shaped" by forcing it to conform to a predetermined shape (e.g. by placing it on a mandrel) followed by performing a stress-relief heat treatment.

Figure 4:
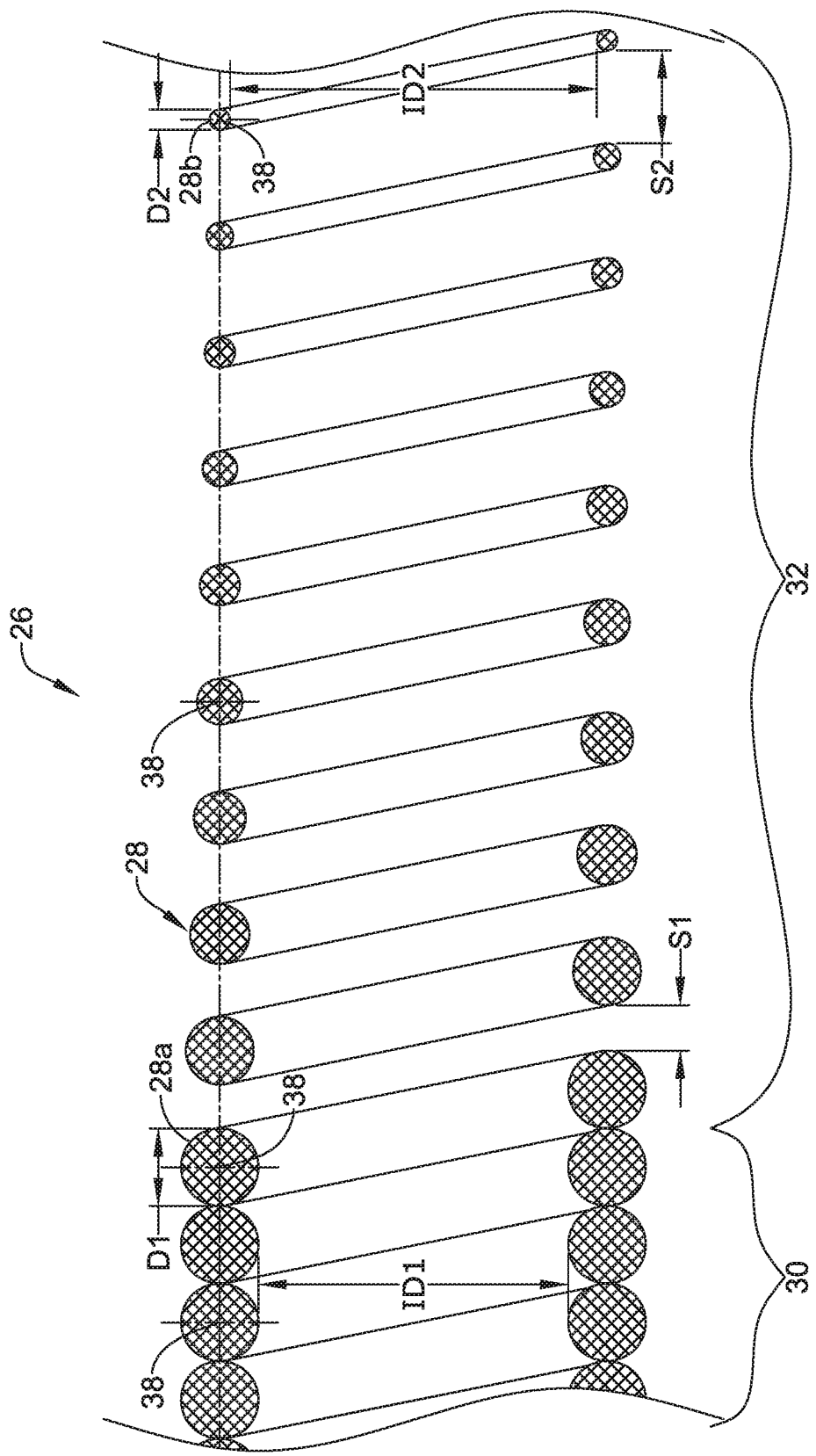
FIG. 4 is a cross-sectional view of a support member useful in the invention showing a reduction in the diameter of the support member.

As seen in FIG. 4, removing material and/or reshaping coil 26 may correspond to a change in its dimensions. FIG. 4 shows an embodiment of coil 26 after having been processed to remove material from filar 28. As shown, coil 26 may be constructed from a single, uninterrupted wire, filament, filar, ribbon or the like. In FIG. 4, filar 28 may have a circular cross-sectional shape. The dashed line in FIG. 4 illustrates that the centroids 38 of filar 28 may be axially-aligned. A centroid 38 may be described as the center point of the cross-section of a given filar 28. It is also contemplated that the cross-sectional shape of filar 28 may be something other than circular. For example, the cross-sectional shape may be triangular, rectangular, oval, or the like. Non-circular shapes may also have centroids that are axially-aligned.

In some instances, filar 28 may have a first filar region 28a and a second filar region 28b. Additionally, after material has been removed from coil 26, filar 28 may have different diameters. For example, FIG. 4 shows diameters D1 and D2 of filar region 28a and 28b, respectively. As can be seen, diameter D1 of filar region 28a is greater than diameter D2 of filar region 28b. The reduced diameter of filar region 28b may be due to a greater amount of material having been removed from filar region 28b versus filar region 28a. In addition to the diameter of filar 28, other dimensions may change as a result of material removal. For example, FIG. 4 shows ID1 and ID2 corresponding to the inner diameter of coil 26 at filar region 28a and 28b, respectively. As shown, inner diameter ID1 of filar region 28a is less than inner diameter ID2 of filar region 28b. The increased inner diameter ID2 of filar region 28b (as compared to ID1 of filar region 28a) can be contributed to the reduction in diameter D2 of filar region 28b (as compared to D1 of filar region 28a).

Additionally, the removal of material may create open space between adjacent windings of filar 28. For example, removing material from a distal portion may create open pitch portion 32. Open pitch portion 32 may be defined as space existing between adjacent windings of filar 28. Depending on the degree to which material is removed, the spacing between adjacent windings of filar 28 may vary. For example, FIG. 4 shows space S1 located proximal of space S2, both of which are located in open pitch portion 32. Further, it can be seen that space S1 is less than S2. The increase in space S2 (as compared to S1) can be contributed to the decrease of diameter D2 of filar region 28b (as compared to diameter D1 of filar region 28a).

As stated above, removal of material may be the result of dipping coil 26 into a processing solution. Therefore, in general, dimensional changes and creation of open space between adjacent windings of filar 28 may result from the up and down dipping process utilized to remove material from coil 26 and/or filar 28. It is also contemplated that the dimensional changes and the extent of open space created may be influenced by the manner in which the process is performed. For example, in some instances the process may include dipping and holding the medical device in the processing solution. In another example process, the medical device may be dipped and/or withdrawn in a stepwise manner.

For example, the medical device may be dipped and held in the processing solution for an initial amount of time. During this initial holding period, an initial amount of material may be removed from the portion of the medical device subject to the processing solution. After this initial holding period, the medical device may be partially withdrawn and held in the processing solution for a second period of time. During the second holding period, additional material may be removed from the portion of the medical device subject to the processing solution. It can be understood that after the second holding period, the outer diameter of the medical device may be different as a result of additional material being removed during the second holding period. Further, this stepwise dipping process may be repeated to achieve the desired stepwise geometry for the medical device. As stated, the particular process implemented may influence the final dimensions, spacing, geometry, etc. of coil 26 and/or filar 28.

In addition to open pitch portion 32, coil 26 may include closed pitch portion 30. Closed pitch portion 30 may correspond to the portion of coil 26 for which no material is removed during a manufacturing process. For example, closed pitch portion 30 may not have been subjected to the dipping process used to remove material from open pitch portion 32. Because no material has been removed from closed pitch portion 30, no space has been created between the windings of filar 28 in closed portion 30.

As can be seen in FIG. 4, the space between filar 28 may gradually increase from closed pitch portion 30 to the distal end of coil 26. The gradual increase in pitch (corresponding to a gradual increase in the amount of material removed from filar 28), may correspond to a progressive change in performance characteristics of coil 26. For example, the flexibility of closed pitch portion 30 may differ from that of open pitch portion 32, due to the dimensional and pitch change of filar 28. Further, the performance characteristics of open cell portion may gradually change from filar region 28a to 28b. For example, the flexibility of open cell portion 32 generally surrounding filar region 28a may be less than the flexibility of closed cell portion 30 generally surrounding filar region 28b.

In some instances, coil 26 may be processed to selectively include or exclude portions of the coil from which material will be removed. For example, portions of coil 26 may be selectively "masked," so that the masked regions of coil 26 are not affected by a material removal manufacturing process. Additionally, coil 26 may be masked in a manner that removes material from different portions of the coil 26 such that the performance of the coil 26 is specifically tailored to a specific application or performance output.

As an alternative embodiment to coil 26 in FIG. 4, FIG. 5 shows coil 126. Similar to coil 26, coil 126 includes filar 128. However, in contrast to filar 28 of FIG. 4, filar 128 may include multiple filar strands 128a, 128b and 128c. Filar strands 128a, 128b and 128c may be braided, woven, twisted, interlaced or the like. Additionally, the centroids of filar 128 of coil 126 may be axially-aligned. Further, as FIG. 5 shows, dimensional changes as a result of material removed from filar 128 may be similar to that discussed with respect to FIG. 4 above.

In some instances, a coil may include multiple filar strands arranged in a configuration as shown in FIG. 5a. For example, FIG. 5a shows six individual filar strands 428a-f configured such that the strands are interwound along the length of coil 426. In this configuration, each individual filar 428a-f has an open pitch (e.g. space between adjacent windings) such that the open space for a given individual filar may be filled by the remaining filar members. For example, FIG. 5a shows coil 426 having six filars, and therefore, an open space defining an open pitch portion may be seen where the space between the windings of each individual filar may be filled by the remaining filars. In other words, the spacing between the individual filars may be approximately equal to the number of filars multiplied by the diameter (or width) of the filars. In FIG. 5a, therefore, the open pitch portion may be equal to the diameter of any one of filars 428a-f multiplied by five. It is contemplated that a coil arrangement may include more or less than the six filars disclosed in FIG. 5a. For example, an example coil may include 1, 2, 3, 4, 5, 6, 7, 8, 9, 10, 11, 12 or more filars.

Additionally or alternatively, a multiple-filar coil may include filars made of different materials and/or having different material properties. Filars constructed of different materials may have different degradation rates and, therefore, different cross-sectional dimensions at a given point in time (e.g., due to different degradation rates). Therefore, a coil having filars made from different materials may exhibit different cross-sectional dimensions (e.g., due to different degradation rates) at different time points during and/or after the processing of the coil. In other instances, the multiple filar coil may include materials with similar or the same degradation rates such that processing may proceed as described herein.

In some instances it may be desirable to configure the cross-sectional shape of a given filar to resemble the cross-sectional diameter of filars 428a-f shown in FIG. 5a. For example, the cross-sectional shape of filars 428a-f may be substantially ovular. Other shapes such as circular, polygonal, or the like are also contemplated. The cross-sectional shape of filars in FIG. 5a may be manufactured by placing the coil on a mandrel and applying an external force and/or swagging to flatten filars 428a-f into the desired (e.g. ovular, etc.) shape.

Figure 5B:
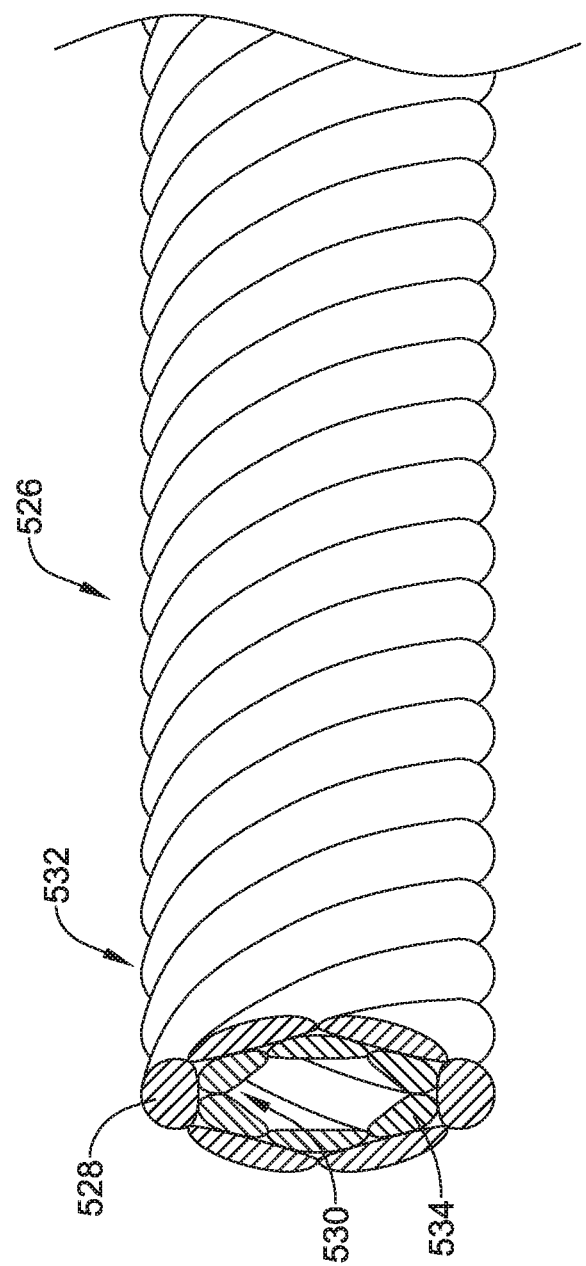
FIG. 5b is a side-view of a multi-strand, multi-layer wire showing flattened cross-sections of individual filars.

In addition to the coil configuration described in FIG. 5a, in some instances it may be desirable to configure a medical device such that the coil includes multiple layers. For example, FIG. 5b shows coil 526 including an inner coil 530 located inside outer coil 532. As shown, the cross-sectional shape of individual outer coil filars 528 of outer coil 532 and inner coil filars 534 of inner coil 530 are configured as described above with respect to filars 428a-f in FIG. 5a. Similar to that of coil 426 of FIG. 5a, coil 526 may be manufactured by placing coil 526 on a mandrel and applying an external force and/or pressure to flatten the individual filars into the desired shape. Additionally, inner and outer coil layers 530/532 may be swaged.

It should be noted that FIGS. 5a-5b disclose coil configurations that may be untreated. It is contemplated that after treating coils disclosed in FIGS. 5a-5b, the coils may resemble the treated coil of FIG. 4. For example, it is contemplated that the coil configurations in FIGS. 5a-5b may have material removed, resulting in an open pitch portion. Further, filars associated with such coils may have a variable pitch opening (e.g. pitch opening increases with decreasing filar diameter) between adjacent filars. Additionally, the filars may have a constant pitch opening between adjacent filars (e.g. pitch opening remains substantially constant as filar diameter decreases). It is also contemplated that after treatment of coils disclosed herein, individual filars may be repositioned such that the desired degree of pitch opening (e.g. constant, variable, etc.) may be obtained.

Figure 6:
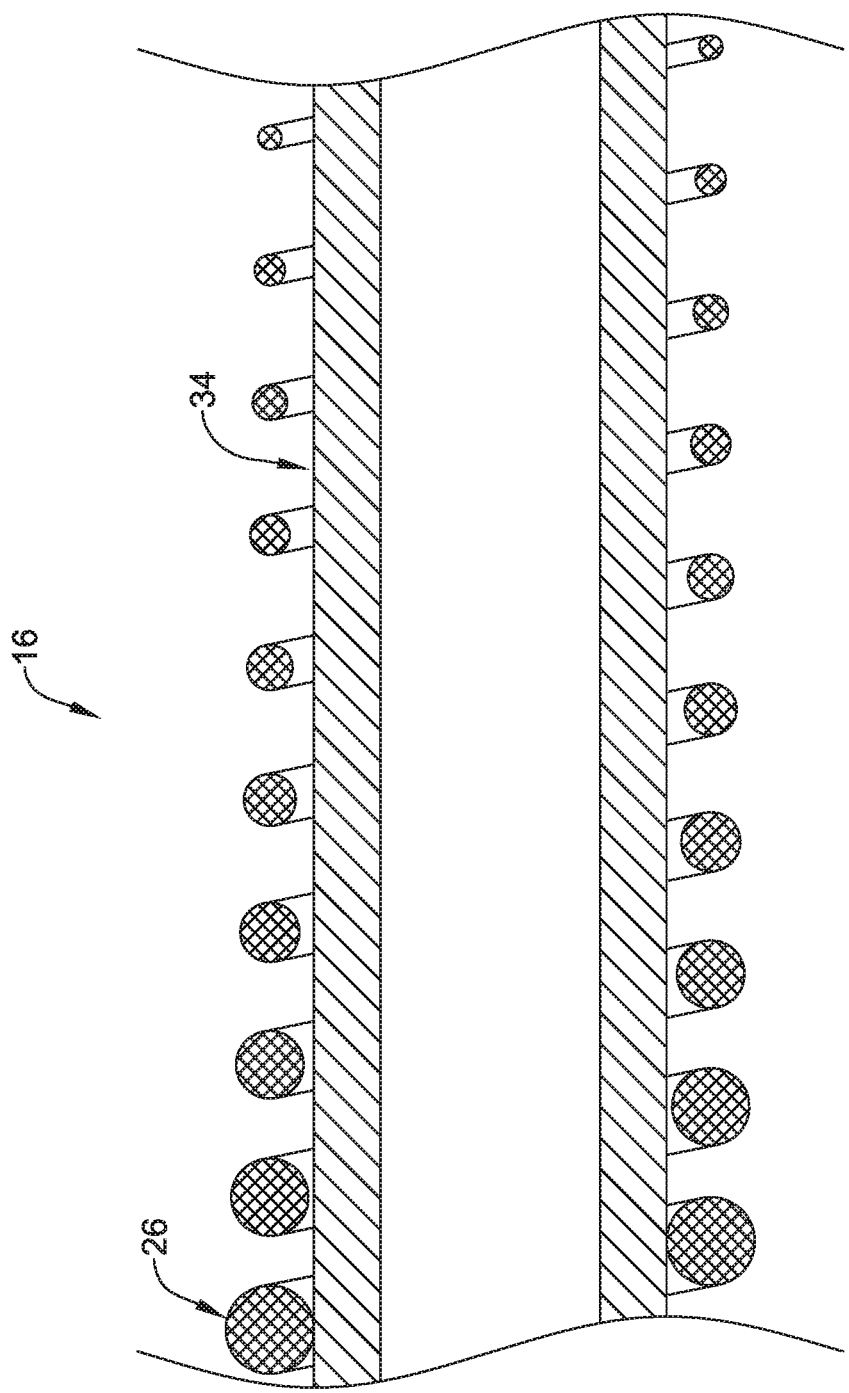
FIG. 6 is a cross-sectional view of a wire disposed over a tubular member.
Figure 7:
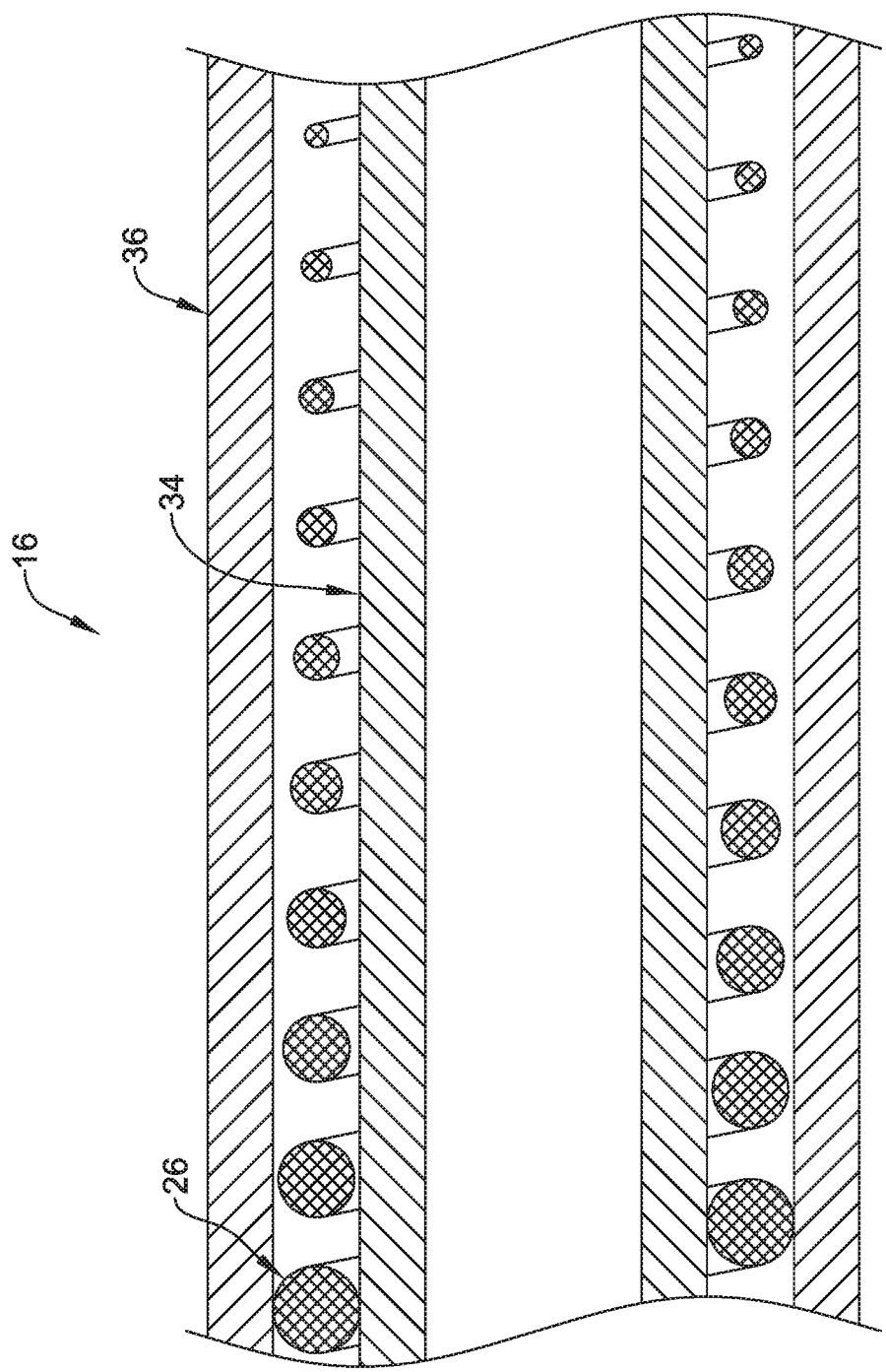
FIG. 7 is a cross-sectional view of a wire disposed between a tubular member and an outer layer.
Figure 8:
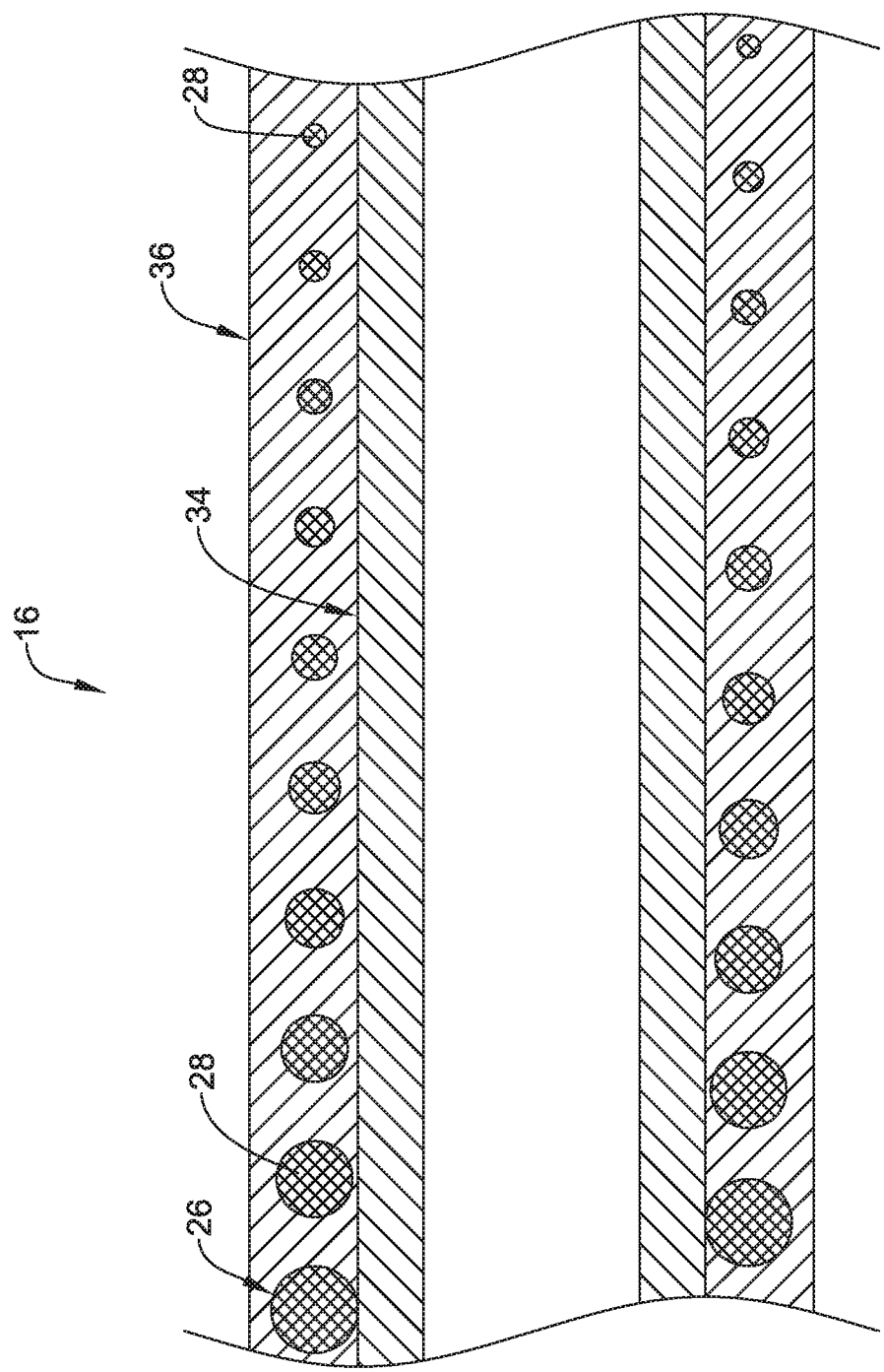
FIG. 8 is a cross-sectional view of a wire embedded in an outer layer.

As suggested herein, it may be desirable to manufacture a number of different medical devices (e.g., guidewire 10, catheter 16, or the like) in a manner that incorporates coil 26. Doing so may provide a number of different desirable characteristics to the resultant device. FIGS. 6-8 show a portion of an example manufacturing process for manufacturing, for example, catheter 16. In this example, catheter 16 incorporates coil 26 into the catheter shaft. The manufacturing process may include disposing coil 26 over a tubular member or shaft 34. Additionally, coil 26 may be placed directly on top of shaft 34. However, it is contemplated that coil 26 may be disposed over shaft 34 while in a tensed state and upon release, coil 26 may "squeeze" down onto shaft 34. In other embodiments, coil 26 may be embedded into shaft 34.

In some instances, shaft 34 may represent a tubular member of catheter 16. For example, shaft 34 may represent the inner member of catheter 16. However, while described herein as an inner shaft, it is contemplated that shaft 34 may include a variety of tubular members. For example, shaft 34 may include a guidewire, polymer tube, elongate member or the like. Additionally, it is contemplated that the combination of coil 26 and shaft 34 may alter the performance properties of catheter 16. For example, the combination of coil 26 and shaft 34 may result in an optimal balance of catheter stiffness and flexibility.

In addition to that described above, it may be desirable to further tailor the performance characteristics of catheter 16 by adding additional materials and/or layers onto existing components. For example, FIG. 7 shows example catheter 16 having incorporated coil 26 onto shaft 34. Further, FIG. 7 shows an additional manufacturing step of incorporating an outer layer 36 into catheter 16. Specifically, outer layer 36 is disposed over coil 26, coil 26 being disposed over shaft 34. In some instances, outer layer 36 may be sit atop coil 26. In other instances, however, outer layer 36 may squeeze down and/or pinch coil 26 onto shaft 34.

Additionally, outer layer 36 may be one or more polymer and/or plastic materials. Further, outer layer 36 may include more than one material. For example, outer layer 36 may include two materials having different material properties (e.g. durometer, tensile strength, etc.). It is also understood that outer layer 36 may include materials other than polymers or plastics. For example, outer layer 36 may include polymers, metals, ceramics, combinations thereof, and the like.

In some instances it may be desirable to further incorporate outer layer 36 with coil 26, sheath 34 or a combination thereof. FIG. 8 shows an example catheter 16 including coil 26, shaft 34 and outer layer 36. Further, outer layer 36 has been processed such that coil 26 is embedded within sheath 36. Additionally, manufacturing catheter 16 such that coil 26 may be embedded in outer layer 36 may require melting and/or reflowing outer layer 36 around coil 26.

As can be seen in FIG. 8, coil 26 may maintain the same configuration as described herein. For example, material may have been progressively removed from filar 28. Further, the centroids of filar 28 may remain axially-aligned before and after manufacturing outer layer 36 to reflow around coil 26.

Figure 9:
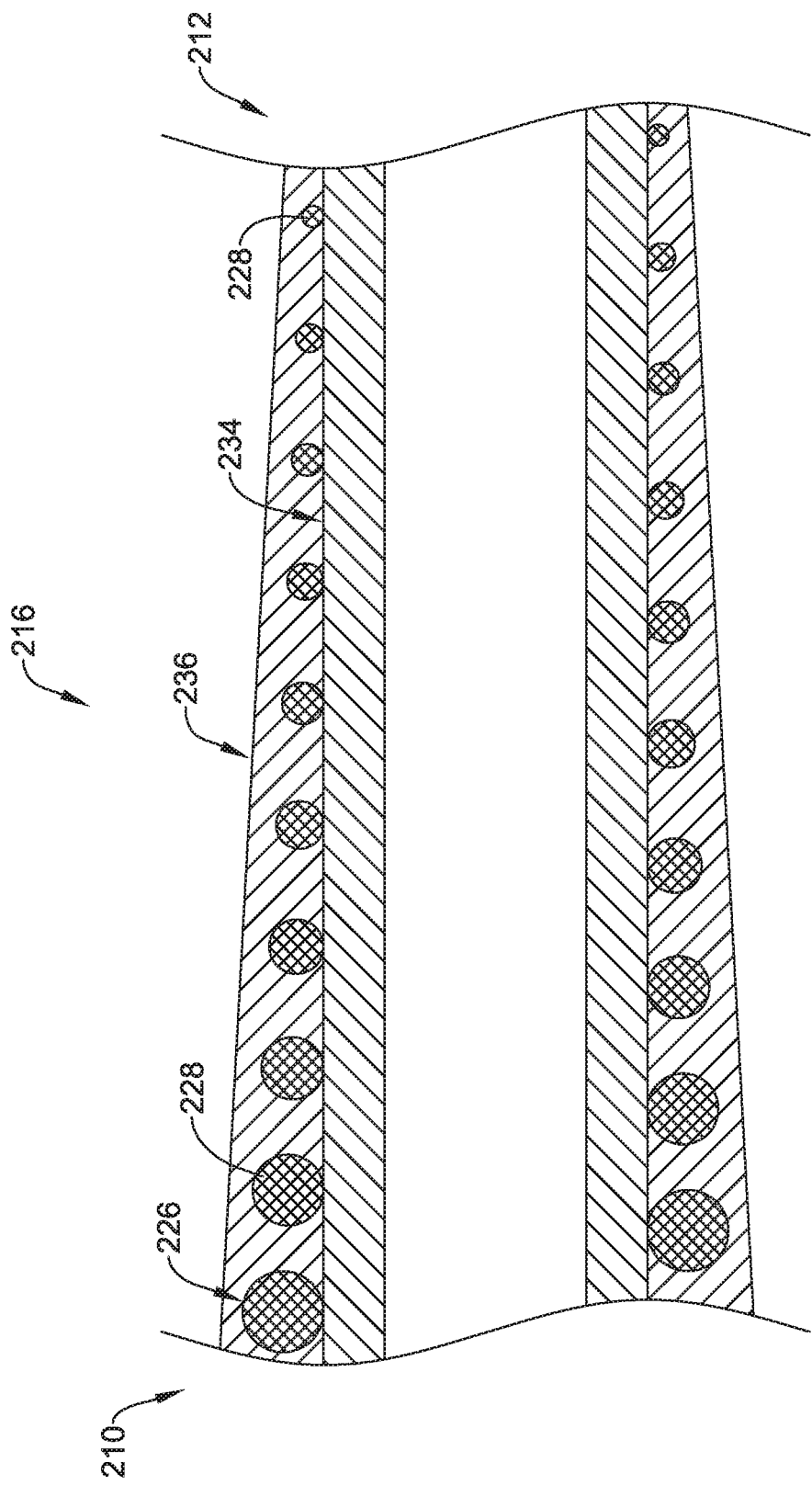
FIG. 9 is a cross-sectional view of a wire disposed over a tubular member and a tapered outer layer.

Reconfiguring the components of catheter 16 disclosed herein may result in different performance outputs. For example, FIG. 9 shows an example catheter 216 including coil 226 disposed along shaft 234 and embedded in sheath 236. However, as FIG. 9 shows, the centroids of filar 228 may not be axially-aligned. Rather, the filar 228 of coil 226 may lie along the surface of shaft 234. In this configuration, the centroid alignment of filar 228 may be tapered with respect to shaft 234. In addition, as shown in FIG. 9, the inner diameter of coil 226 may be substantially uniform along the surface of shaft 234. For example, pressure may be applied to filar 228 in order to shift filar 228 so that the inner diameter remains uniform.

Further, in some instances it may be desirable to modify the outer profile of catheter 216. For example, outer layer 236 may be tapered from a proximal to distal direction. As shown in FIG. 9, the outer diameter of proximal portion 210 of catheter 216 is greater than the outer diameter of distal portion 212. However, while FIG. 9 shows outer layer 236 tapering in from a proximal to distal direction, it is contemplated that other configurations may be desirable.

Figure 10:
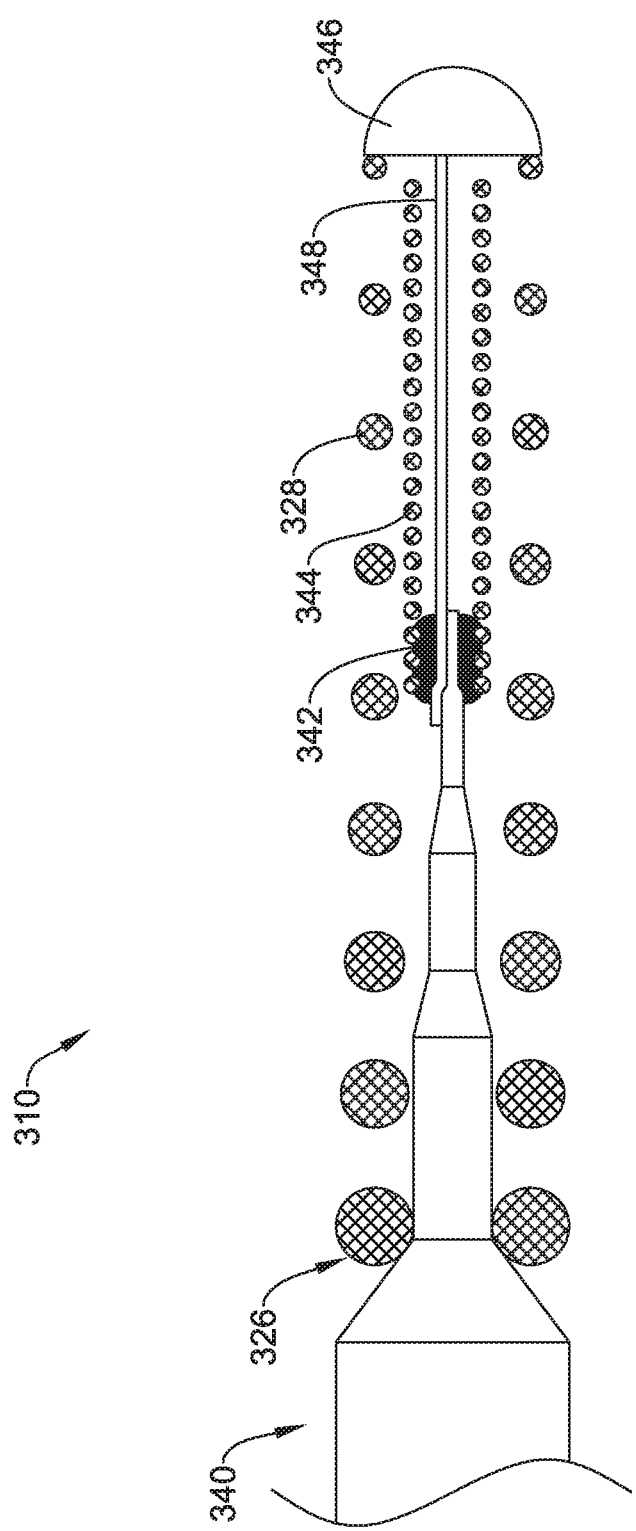
FIG. 10 is a cross-sectional view of a wire incorporated into a medical device.

FIG. 10 shows example guidewire 310 incorporating coil 326. In some instances, guidewire 310 may include a radiopaque coil 344 attached to a core wire 340 by a weld 342. Further, a proximal portion of coil 326 may be attached to core wire 340 and a distal portion of coil 326 may be attached to tip portion 346. Tip portion 346 may also be attached to a ribbon 348. Coil 326 may be configured according to any of the embodiments disclosed herein. For example, FIG. 10 shows the centroids of filar 328 of coil 326 axially-aligned over the length of coil 326. In other examples, the centroids of the filar 328 may not be axially-aligned. Additionally, coil 326 may be coated and/or include a sheath or covering.

The materials that can be used for the various components of guidewire 10 (and/or other guidewires disclosed herein) and the various tubular members disclosed herein may include those commonly associated with medical devices. For simplicity purposes, the following discussion makes reference to catheter 16 and other components of guidewire 10. However, this is not intended to limit the devices and methods described herein, as the discussion may be applied to other similar medical devices and/or components of medical devices disclosed herein.

Catheter 16 and/or other components of guidewire 10 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C -22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of catheter 16 and/or guidewire 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into guidewire 10. For example, catheter 16 and/or guidewire 10, or portions thereof, may be made of a material that does not substantially distort the image and create substantial artifacts (i.e., gaps in the image). Certain ferromagnetic materials, for example, may not be suitable because they may create artifacts in an MRI image. Catheter 16 and/or guidewire 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A catheter comprising:
a tubular elongate shaft having a distal region and a lumen extending therethrough;
a coil surrounding an outer surface of the distal region of the tubular elongate shaft, wherein the coil is formed from one or more filars forming a plurality of windings;
wherein the coil has a first filar region and a second filar region, the first filar region extending to a proximal end of the coil, and the second filar region extending to a distal end of the coil;
wherein each filar of the one or more filars has a first cross-sectional diameter along the first filar region and a second cross-sectional diameter along the second filar region, the second cross-sectional diameter being less than the first cross-sectional diameter;
wherein each filar of the one or more filars has a cross-sectional area having a first centroid at a first position along the first filar region and a cross-sectional area having a second centroid at a second position along the second filar region, the second centroid being positioned closer to a central longitudinal axis of the tubular elongate shaft than the first centroid;
wherein the coil has a closed pitch in the first filar region in which there is no space between adjacent windings of the plurality of windings, and the coil has an open pitch in the second filar region in which there is spacing between adjacent windings of the plurality of windings;
and wherein the spacing between adjacent windings of the plurality of windings increases in a distal direction along the second filar region;

wherein a first longitudinal distance between centroids of adjacent windings of the plurality of windings in the first filar region is equal to a second longitudinal distance between centroids of adjacent windings of the plurality of windings in the second filar reqion.

2. The catheter of claim 1, wherein each winding contacts the outer surface of the tubular elongate shaft.

3. The catheter of claim 1, wherein a first radial distance between the central longitudinal axis and the first filar region is the same as a second radial distance between the central longitudinal axis and the second filar region.

4. The catheter of claim 1, further comprising a polymeric outer layer surrounding and in contact with the coil.

5. The catheter of claim 4, wherein the one or more filars are embedded in the polymeric outer layer in the second filar region.

6. The catheter of claim 5, wherein the polymeric outer layer has an outer diameter that tapers radially inward in a distal direction along the second filar region.

7. The catheter of claim 5, wherein the polymeric outer layer contacts the tubular elongate shaft between adjacent windings of the plurality of windings in the second filar region.

8. The catheter of claim 1, wherein the coil has a first outer diameter along the first filar region and a second outer diameter along the second filar region, the second outer diameter being less than the first outer diameter.

9. A catheter, comprising:
a tubular elongate shaft having a distal region and a lumen extending therethrough;
a coil surrounding an outer surface of the distal region of the tubular elongate shaft, wherein the coil is formed from one or more filars forming a plurality of windings;
wherein the coil has a first filar region and a second filar region, the first filar region extending to a proximal end of the coil, and the second filar region extending to a distal end of the coil;
wherein each filar of the one or more filars has a first cross-sectional diameter along the first filar region and a second cross-sectional diameter along the second filar region, the second cross-sectional diameter being less than the first cross-sectional diameter;
wherein each filar of the one or more filars has a cross-sectional area having a first centroid at a first position along the first filar region and a cross-sectional area having a second centroid at a second position along the second filar region, wherein a first longitudinal distance between centroids of adjacent windings of the plurality of windings in the first filar region is equal to a second longitudinal distance between centroids of adjacent windings of the plurality of windings in the second filar region;
wherein the coil has a closed pitch in the first filar region in which there is no space between adjacent windings of the plurality of windings, and the coil has an open pitch in the second filar region in which there is spacing between adjacent windings of the plurality of windings;
and wherein the spacing between adjacent windings of the plurality of windings increases in a distal direction along the second filar region.

10. The catheter of claim 9, further comprising a polymeric outer layer surrounding and in contact with the coil.

11. The catheter of claim 10, wherein the one or more filars are embedded in the polymeric outer layer in the second filar region.

12. The catheter of claim 11, wherein the polymeric outer layer contacts the tubular elongate shaft between adjacent windings of the plurality of windings in the second filar region.

13. The catheter of claim 9, wherein the first filar region includes a first filar inner diameter and the second filar region includes a second filar inner diameter and wherein the first filar inner diameter is less than the second filar inner diameter.

14. The catheter of claim 9, wherein the first filar region includes a first filar inner diameter and the second filar region includes a second filar inner diameter and wherein the first filar inner diameter is the same as the second filar inner diameter.

15. The catheter of claim 9, wherein the coil has a first outer diameter at the first position along the first filar region, and wherein the coil has a second outer diameter less than the first outer diameter at the second position along the second filar region.

16. The catheter of claim 9, wherein the second centroid is positioned radially closer to the tubular elongate shaft than the first centroid.

17. A catheter comprising:
a tubular elongate shaft having a distal region and a lumen extending therethrough;
a coil extending along the distal region of the tubular elongate shaft, wherein the coil is formed from a plurality of filars wrapped around the tubular elongate shaft;
wherein the coil has a first filar region and a second filar region, the first filar region extending to a proximal end of the coil, and the second filar region extending to a distal end of the coil;
wherein each filar of the plurality of filars has a first cross-sectional diameter along the first filar region and a second cross-sectional diameter along the second filar region, the second cross-sectional diameter being less than the first cross-sectional diameter;
wherein each filar of the plurality of filars has a cross-sectional area having a first centroid at a first position along the first filar region and a cross-sectional area having a second centroid at a second position along the second filar region, the second centroid being positioned closer to a central longitudinal axis of the tubular elongate shaft than the first centroid;
wherein the coil has a first spacing between adjacent filars in the first filar region and the coil has second spacing between adjacent filars in the second filar region that is greater than the first spacing;
and wherein the second spacing increases in a distal direction along the second filar region;
wherein the centroids of adjacent windings of the plurality of filars are equally spaced along an entire length of the coil.

18. The catheter of claim 17, wherein the second cross-sectional diameter decreases in a distal direction along the second filar region.

19. The catheter of claim 17, wherein the coil has a first outer diameter along the first filar region and a second outer diameter along the second filar region, the second outer diameter being less than the first outer diameter.

* * * * *